United States Patent [19]

Krämer et al.

[11] 4,255,434
[45] Mar. 10, 1981

[54] COMBATTING FUNGI WITH 1-(AZOL-1-yl)-4-HALO-(1)-PHENOXY-BUTAN-2-ONES AND -OLS

[75] Inventors: Wolfgang Krämer; Karl Büchel, both of Wuppertal; Paul-Ernst Frohberger, Leverkusen; Wilhelm Brandes, Cologne; Hans Scheinpflug, Leverkusen, all of Fed. Rep. of Germany

[73] Assignee: Bayer Aktiengesellschaft, Leverkusen, Fed. Rep. of Germany

[21] Appl. No.: 964,215

[22] Filed: Nov. 27, 1978

Related U.S. Application Data

[63] Continuation-in-part of Ser. No. 816,975, Jul. 19, 1977, abandoned.

[30] Foreign Application Priority Data

Jul. 20, 1976 [DE] Fed. Rep. of Germany ....... 2632602
Jul. 20, 1976 [DE] Fed. Rep. of Germany ....... 2632603

[51] Int. Cl.$^3$ .................. A01N 43/50; A01N 43/48; C07D 233/60; C07D 249/08
[52] U.S. Cl. .................. 424/269; 424/273 R; 424/232; 548/262; 548/341; 568/308; 568/315; 568/325; 568/391; 568/392; 568/414; 568/419
[58] Field of Search .................. 260/308 R; 548/341, 548/262; 424/269, 273

[56] References Cited

U.S. PATENT DOCUMENTS

| | | | |
|---|---|---|---|
| 3,812,142 | 5/1974 | Meiser et al. | 548/341 |
| 3,912,752 | 10/1975 | Meiser et al. | 260/308 R |
| 3,940,414 | 2/1976 | Kramer | 548/341 |
| 3,952,002 | 4/1976 | Kramer et al. | 424/269 |
| 3,972,891 | 8/1976 | Kramer | 260/308 R |
| 4,000,299 | 12/1976 | Kramer et al. | 424/273 |
| 4,013,677 | 3/1977 | Stolzer et al. | 260/308 R |

OTHER PUBLICATIONS

Harsfall, Fungicides and Their Action, (Waltham, Mass., U.S.A., 1945), pp. 151-152.

*Primary Examiner*—Alton D. Rollins
*Attorney, Agent, or Firm*—Sprung, Felfe, Horn, Lynch & Kramer

[57] ABSTRACT

Fungicidal 1-(azol-1-yl)-4-halo-1-phenoxy-butan-2-ones and -ols of the formula

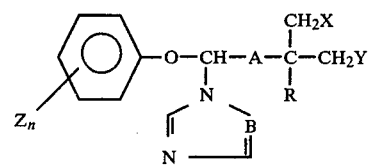

in which
R represents alkyl with 1 to 4 carbon atoms;
X represents hydrogen, alkyl with 1 to 4 carbon atoms or halogen;
Y represents halogen;
Z represents halogen, straight-chain or branched alkyl with 1 to 4 carbon atoms, cycloalkyl with 5 to 7 carbon atoms, halogenoalkyl with 1 or 2 carbon atoms and 1 to 5 halogen atoms, alkoxy with one or 2 carbon atoms, alkylthio with 1 or 2 carbon atoms, alkoxycarbonyl with 1 to 5 carbon atoms in the alkoxy part, amino, cyano, nitro, phenyl or phenoxy substituted with at least one of halogen, amino, cyano, nitro and alkyl with 1 to 2 carbon atoms, phenylalkyl with 1 or 2 carbon atoms on the alkyl part optionally substituted in the alkyl part by alkylcarbonyl with a total of up to 3 carbon atoms and in the phenyl part by halogen, nitro or cyano;
n represents 0,1,2 or 3,
A is —CO— or CH(OH)—, and
B is —N= or —CH=, or a salt thereof.

10 Claims, No Drawings

COMBATTING FUNGI WITH 1-(AZOL-1-YL)-4-HALO-(1)-PHENOXY-BUTAN-2-ONES AND -OLS

This is a continuation-in-part of application Ser. No. 816,975, filed July 19, 1977, now abandoned.

The present invention relates to and has for its objects the provision of particular new 1-(azol-1-yl)-4-halo-1-phenoxybutan-2-ones and -ols which possess fungicidal properties, active compositions in the form of mixtures of such compounds with solid and liquid dispersible carrier vehicles, and methods for producing such compounds in a new way especially for combating pests, e.g. fungi, with other and further objects becoming apparent from a study of the within specification and accompanying examples.

It has been disclosed in U.S. Pat. Nos. 3,898,341, 3,912,752, 3,940,414 and 3,952,002 that certain 1,2,4-triazole derivatives such as 3,3-dimethyl-1-phenoxy-1-(1,2,4-triazol-1-yl)-butan-2-ones and -ols which are substituted on the phenyl ring, imidazole derivatives such as 3,3-dimethyl-1-(imidazol-1-yl)-1-phenoxy-butan-2-ones and -ols which are substituted on the phenyl ring, and ω-(imidazol-1-yl) ω-phenoxy-acetophenones which are substituted on the pehenoxy ring, exhibit good fungicidal properties. However, the activity of the previously known compounds is not always entirely satisfactory, especially when low amounts and low concentrations are used.

The present invention now provides, as new compounds, the halogenated 1-azolyl-butane derivatives of the general formula

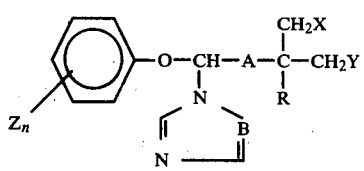

in which
R is alkyl, phenyl or substituted phenyl,
X is hydrogen, alkyl or halogen,
Y is halogen,
Z is halogen, alkyl, cycloalkyl, alkoxy, halogenoalkyl, alkylthio, alkoxycarbonyl, amino, cyano, nitro, phenyl, phenoxy, phenylalkyl, or substituted phenyl, phenoxy or phenylalkyl,
n represents 0, 1, 2, 3, 4 or 5,
A is —CO— or —CH(OH)—, and
B is —N= or CH=, and their salts.

The compounds of the present invention exhibit powerful fungicidal properties.

Preferably, R represents alkyl with 1 to 4 carbon atoms (especially methyl or ethyl) or phenyl which is optionally substituted by halogen (especially fluorine, chlorine or bromine) and/or alkyl with 1 or 2 carbon atoms;

X represents hydrogen, alkyl with 1 to 4 carbon atoms (especially methyl) or halogen (especially chlorine or bromine);

Y represents halogen (especially chlorine or bromine);

Z represents halogen (namely fluorine, chlorine, bromine or iodine), straight-chain or branched alkyl with 1 to 4 carbon atoms, cycloalkyl with 5 to 7 carbon atoms (preferably cyclohexyl), halogenoalkyl with 1 or 2 carbon atoms and 1 to 5 halogen atoms (especially fluorine and chlorine atoms, the trifluoromethyl group being an example), alkoxy with 1 or 2 carbon atoms, alkylthio with 1 or 2 carbon atoms, alkoxycarbonyl with 1 to 5 carbon atoms in the alkoxy part, amino, cyano, nitro, or optionally substituted phenyl or phenoxy, the substituents being selected from halogen (namely fluorine, chlorine, bromine or iodine), amino, cyano, nitro and alkyl with 1 to 2 carbon atoms or Z represents phenylalkyl with 1 or 2 carbon atoms in the alkyl part and which may be substituted in the alkyl part by alkylcarbonyl with a total of up to 3 carbon atoms and which may be substituted in the phenyl part by halogen, nitro or cyano; and n represents 0, 1, 2 or 3.

Those compounds of the formula (I) in which A represents a CH(OH) group possess two asymmetrical carbon atoms; they can therefore exist in the two geometric isomers (erythro form and threo form), which may be produced in different ratios. In both cases they exist as optical isomers. The formula (I) should be construed as covering all such isomers.

Furthermore, the halogenated 1-azolyl-butane derivatives obtainable according to the invention can be converted to the salts by reaction with acids.

Preferred salts of the compounds of the formula (I) are (from the point of view of phytotoxicity) the physiologically tolerated salts, these being generally salts with physiologically tolerated acids. The preferred acids include the hydrogen halide acids (such as, for example, hydrobromic acid and especially hyrochloric acid), phosphoric acid, nitric acid, monofunctional and bifunctional carboxylic acids and hydroxycarboxylic acids (such as, for example, acetic acid, maleic acid, succinic acid, fumaric acid, tartaric acid, salicylic acid, citric acid, sorbic acid and lactic acid) and 1,5-naphthalenedisulphonic acid.

Conversely, the acid-addition salts can be treated with a base to liberate, if desired, the free base of the formula (I).

Surprisingly, the active compounds according to the invention exhibit a substantially higher fungicidal activity, especially against species of rust and species of mildew, as well as against rice diseases, than the 3,3-dimethyl-1-phenoxy-1-(1,2,4-triazol-1-yl)-butan-2-ones and -ols, the corresponding imidazolyl derivatives and the ω-(imidazol-1-yl)-ω-phenoxy-acetophenones known from the prior art, which are the closest active compounds of the same type of action. The active compounds according to the invention thus represent an enrichment of the art.

The present invention also provides a process for the preparation of a halogenated 1-azolylbutane derivative of the formula (I), in which (a) a bromoether-ketone of the general formula

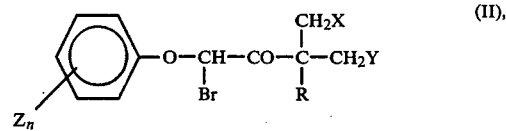

in which
R, X, Y, Z and n have the above-mentioned meanings, is reacted with an azole of the general formula

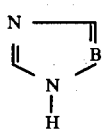

in which

B has the above-mentioned meaning, if appropriate in the presence of an acid-burning agent and, if appropriate, in the presence of a diluent, and optionally thereafter (b) the keto-derivative obtained according to process variant (a) is (1) reduced with hydrogen in the presence of a catalyst and optionally in the presence of a polar solvent, or (2) reduced with aluminum isopropylate in the presence of a solvent, or (3) reduced with a complex hydride, optionally in the presence of a polar solvent, or (4) reduced with formamidinesulphinic acid and an alkali metal hydroxide, optionally in the presence of a polar solvent.

If 1-bromo-4-chloro-1-(4-chlorophenoxy)-3,3-dimethylbutan-2-one and 1,2,4-triazole are used as starting materials in process variant (a), the course of the reaction can be represented by the following equation:

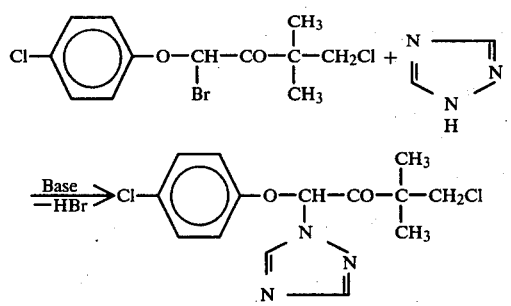

If, on the other hand, 1-bromo-4-chloro-1-(4-chlorophenoxy)-3,3-dimethyl-butan-2-one and imidazole are used as starting materials, the course of the reaction can be represented by the following equation:

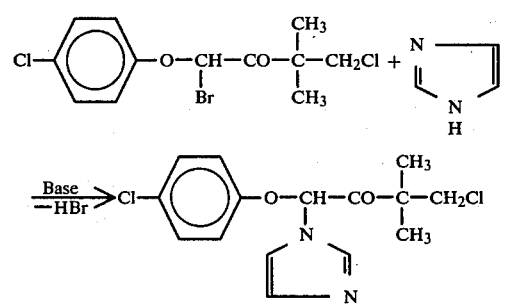

If 4-chloro-1-(4-chlorophenoxy)-3,3-dimethyl-1-(1,2,4-triazol-1-yl)-butan-2-one and sodium borohydride are used as starting materials in process variant (b)(3), the course of the reaction can be represented by the following equation:

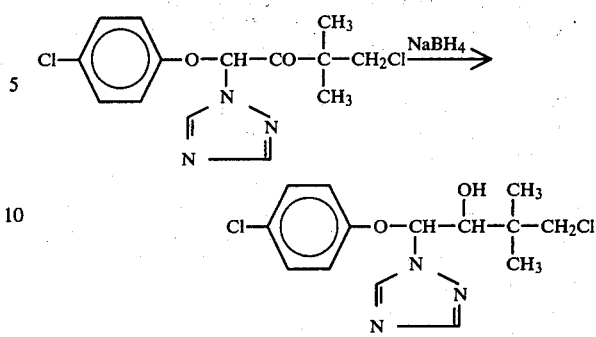

If, on the other hand, 4-chloro-1-(4-chlorophenoxy)-3,3-dimethyl-1-(imidazol-1-yl)-butan-2-one and sodium borohydride are used as starting materials, the course of the reaction can be represented by the following equation:

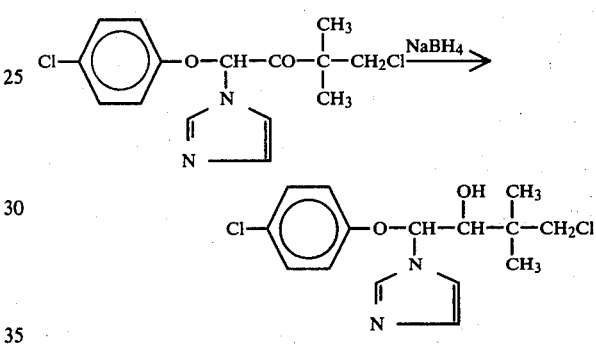

The reduction reactions according to process variants (b)(1), (b)(2) and (b)(4) are of a similar type and can be formulated analogously.

The following may be mentioned as examples of starting materials of the formula (II): 1-bromo-4-chloro-1-(3-chlorophenoxy)-3,3-dimethyl-butan-2-one, 1-bromo-4-chloro-3,3-dimethyl-1-(4-fluorophenoxy)-butan-2-one, 1-bromo-4-chloro-3,3-dimethyl-1-(4-iodophenoxy)-butan-2-one, 1-bromo-1-(4-bromophenoxy)-4-chloro-3,3-dimethyl-butan-2-one, 1-bromo-4-chloro-3,3-dimethyl-1-(2,4,5-trichlorophenoxy)-butan-2-one, 1-bromo-4-chloro-3,3-dimethyl-1-(2-methylphenoxy)-butan-2-one, 1-bromo-4-chloro-3,3-dimethyl-1-(4-methylphenoxy)-butan-2one, 1-bromo-4-chloro-3,3-dimethyl-1-(3,4-dimethylphenoxy)-butan-2-one, 1-bromo-4-chloro-1-(4-chloro-2-methylphenoxy)-3,3-dimethyl-butan-2-one, 1-bromo-4-chloro-1-(4-chloro-3,5-dimethylphenoxy)-3,3-dimethyl-butan-2one, 1-bromo-4-chloro-3,3-dimethyl-1-(2-methyl-5-nitrophenoxy)-butan-2-one, 1-bromo-4-chloro-1-(2-cyclohexylphenoxy)-3,3-dimethyl-butan-2-one, 1-bromo-4-chloro-1-(4-cyclohexylphenoxy)-3,3-dimethyl-butan-2-one, 1-bromo-4-chloro-3,3-dimethyl-1-(4-methoxyphenoxy)-butan-2-one, 1-bromo-4-chloro-3,3-dimethyl-1-(3-trifluoromethylphenoxy)-butan-2-one, 1-bromo-4-chloro-3,3-dimethyl-1-(4-methylthiophenoxy)-butan-2-one, 1-bromo-4-chloro-3,3-dimethyl-1-(4-methoxycarbonylphenoxy)-butan-2-one, 1-bromo-4-chloro-3,3-dimethyl-1-(2-phenylphenoxy)-butan-2-one, 1-bromo-4-chloro-1-(2-chloro-4-phenylphenoxy)-3,3-dimethyl-butan-2-one, 1-bromo-4-chloro-[4-(4'-chlorophenoxy)-phenoxy]-3,3-dimethyl-butan-2-one, 1- bromo-1-[4-(4′-chlorobenzyl)-phenoxy]-3,3-dimethyl-butan-2-one, 1-bromo-4-chloro-1-[4-(phenyl-acetyloxy-methyl)-phenenoxy]-3,3-dimethyl-butan-2-one, 1-bromo-4-chloro-1-(4-cyanophenoxy)-3,3-dimethyl-butan-2-one, 1-(4-aminophenoxy)-1-bromo-4-chloro-3,3-dimethyl-butan-2-one, 1-(4-chlorophenoxy)-1,4-dibromo-3,3-dimethyl-butan-2-one, 1-bromo-4-chloro-1-(4-chlorophenoxy)-3,3-diethyl-butan-2-one, 1-bromo-4-chloro-3-chloromethyl-1-(4-chlorophenoxy)-3-methyl-butan-2-one and 1-bromo-4-chloro-3-chloromethyl-1-(4-chlorophenoxy)-3-(4-chlorophenyl)-butan-2-one.

The bromoether-ketones of the formula (II) to be used as starting materials according to the invention can be prepared in accordance with known processes, for example by reacting phenols of the general formula

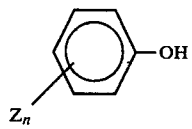

(III), in which

Z and n have the above-mentioned meanings, with a bromoketone of the formula

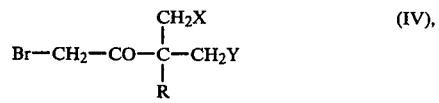

(IV), in which

R, X and Y have the above-mentioned meanings. The active hydrogen atom which still remains is then replaced by bromine in the usual manner, as shown in the preparative examples hereinbelow.

The phenols of the formula (III) are compounds generally known in organic chemistry.

The bromoketones of the formula (IV) are also compounds which are generally known in organic chemistry or can be prepared in the generally customary and known manner (see also the preparative examples.

The azoles (V) to be used as starting materials for process (a) are 1,2,4-triazole and imidazole.

Possible diluents for the reaction according to process variant (a) are inert organic solvents, especially ketones, such as diethyl ketone and especially acetone and methyl ethyl ketone; nitriles, such as propionitrile and especially acetonitrile; alcohols, such as ethanol or isopropanol; ethers, such as tetrahydrofuran or dioxane; benzene; formamides, such as, in particular, dimethylformamide; and halogenated hydrocarbons.

If the reaction according to process variant (a) is carried out in the presence of an acid-binding agent, all inorganic and/or organic acid-binding agents which can usually be employed may be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylmethylamine and N,N-dimethylbenzylamine, and also pyridine and diazabicyclooctane.

Preferably, however, an appropriate excess of the azole is used as the acid acceptor.

In process variant (a), the reaction temperatures can be varied within a substantial range. In general, the reaction is carried out at from 20° to 150° C., preferably at from 60° to 120° C. In the presence of a solvent, the reaction is advantageously carried out at the boiling point of the particular solvent.

In carrying out process variant (a), preferably 2 moles of the azole and 1 to 2 moles of acid-binding agent are employed per mole of the compound of the formula (II). To isolate the compound of the formula (I), the solvent is distilled off and the residue is taken up in an organic solvent and washed with water. The organic phase is dried over sodium sulphate and freed from the solvent in vacuo. The residue is purified by distillation or recrystallization.

Possible diluents for the reaction according to process variant (b)(1) are polar organic solvents, preferably alcohols, such as methanol and ethanol, and nitriles, such as acetonitrile. The reaction is carried out in the presence of a catalyst. Preferably, noble metal catalysts, noble metal oxide (or noble metal hydroxide) catalysts or so-called "Raney catalysts" are used, especially platinum, platinum oxide and nickel. The reaction temperatures can be varied within a substantial range. In general, the reaction is carried out at from 20° to 50° C., preferably at from 20° to 40° C. The reaction can be carried out not only under normal pressure, but also under elevated pressure (for example 1 or 2 atmospheres gauge). In the reaction according to process variant (b)(1), 1 mole of hydrogen and 0.1 mole of catalyst are preferably employed per mole of the compound of the formula (II); to isolate the product, the catalyst is filtered off, the filtrate is freed from the solvent in vacuo and the resulting compound of the formula (I) is purified by distillation or recrystallization.

If process variant (b)(2) is followed, preferred diluents for the reaction are alcohols, such as isopropanol, or inert hydrocarbons, such as benzene. The reaction temperatures can again be varied within a substantial range; in general, the reaction is carried out at from 20° to 120° C., preferably at 50° to 100° C. To carry out the reaction, 1 to 2 moles of aluminum isopropylate are preferably employed per mole of the compound of the formula (II).

To isolate the compounds of the formula (I), the excess solvent is removed by distillation in vacuo and the resulting aluminum compound is decomposed with dilute sulphuric acid or sodium hydroxide solution. The further working up is carried out in the usual manner.

If process variant (b)(3) is followed, possible diluents for the reaction are polar organic solvents, especially alcohols, such as methanol, ethanol, butanol or isopropanol, and ethers, such as diethyl ether or tetrahydrofuran. The reaction is in general carried out at from 0° to 30° C., preferably at 0° to 20° C. For this reaction, preferably 1 mole of a complex hydride, such as sodium borohydride or lithium aluminum hydride, is employed per mole of the compound of the formula (II). To isolate the compounds of the formula (I), the residue is taken up in dilute hydrochloric acid, then rendered alkaline and extracted with an organic solvent. The further working up is carried out in the usual manner.

Possible diluents for the reaction according to variant (b)(4), are polar organic solvents, preferably alcohols, such as methanol and ethanol, and also water. Here again the reaction temperatures can be varied within a substantial range; the reaction is in general carried out at temperatures from 20° to 100° C., preferably at 50° to 100° C. To carry out the reaction, 1 to 3 moles of formamidinesulphinic acid and 2 to 3 moles of alkali metal hydroxide are generally employed per mole of the compound of the formula (II). To isolate the end product, the reaction mixture is freed from the solvent and the residue is extracted with water and organic solvents, worked up in the usual manner and purified.

The active compounds according to the invention exhibit a powerful fungitoxic action and a bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seedborne pathogens.

They display a particularly good activity against parasitic fungi on above-ground parts of plants, such as species of Erysiphe, species of Podosphaera and species of Venturia, and also against species of Pyricularia and species of Pellicularia. Good actions are achieved against the pathogens of apple mildew (*Podospharea leucotricha*), apple scab (*Fusicladium dendriticum*), powdery mildew of cucumbers (*Erysiphe cichoracearum*) and bean rust (*Uromyces phaseoli*), as well against the fungi *Pyricularia oryzae* and *Pellicularia sasakii*. They furthermore exhibit a high activity against cereal diseases, such as against cereal mildew and cereal rust. An aspect to be singled out particularly is that the active compounds according to the invention not only display a protective action but are also curatively active, that is to say are active when used after infection has taken place. Furthermore, the fact that in part a systemic action is found should be pointed out. Thus it proves possible to protect plants against fungal attack by supplying the active compound to the above-ground parts of the plant through the soil and the root, or through the seed.

As plant protection agents, the compounds according to the invention can be used for the treatment of soil, for the treatment of seed and for the treatment of above-ground parts of plants.

The compounds according to the invention are well tolerated by plasts. They have only a low toxicity to warm-blooded animals and, because of their low odor and their good toleration by human skin, they are not unpleasant to handle.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usuable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane and trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cylcohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl ar polyglycol ethers, magnesium stearate, sodium oleate, etc.); and/or dispersing agents, such as lignin, sulfite waster liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematocides, bactericides, rodenticides, herbicides, fertilizers, growth-regulating agents, bird repellents, plant nutrients, agents for improving soid structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier compositions mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance along, e.g. about 20–100% by weight of the active compound.

Especially when used as leaf fungicides, the active compound concentrations in the use forms can be varied within a substantial range. They are, in general, from 0.1 to 0.00001 percent by weight, preferably from 0.05 to 0.0001 percent.

For the treatment of seed, amounts of active compound of 0.001 to 50 g per kilogram of seed, preferably 0.01 to 10 g, are generally employed.

For the treatment of soil, amounts of 1 to 1,000 g per cubic meter of soil, preferably of 10 to 200 g, are generally employed.

If appropriate amounts are used, the compounds according to the invention also exhibit a growth-regulating activity.

Furthermore, the present invention contemplates methods of selectively killing, combatting or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurring dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

(a)

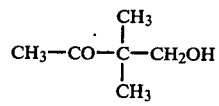

66 g (2.2 mol) of paraformaldehyde and 1 g of potassium hydroxide in 10 ml of methanol were added dropwise to 172 g (2 mol) of methyl isopropyl ketone in 1,000 ml of methanol. The mixture was heated for 15 hours under reflux and the methanol was then distilled off through a column, at 82° C. internal temperature. The residue was distilled in a waterpump vacuum. 152.7 g (68% of theory) of 2,2-dimethyl-1-hydroxy-butan-3-one of boiling point 80°–82° C./12 mm Hg were obtained.

(b)

(i)

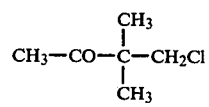

11.6 g (0.1 mol) of 2,2-dimethyl-1-hydroxy-butan-3-one were added dropwise at 50° to 60° C. (while cooling with ice) to 20.5 g (0.1 mol) of N,N-diethyl-1,2,2-trichlorovinylamine. After stirring for two hours at 60° C., the mixture was distilled in a waterpump vacuum. 8.1 g (60% of theory) of 1-chloro-2,2-dimethyl-butan-3-one of melting point 60°–62° C./12 mm Hg were obtained.

(ii)

1-Chloro-2,2-dimethyl-butan-3-one was obtained in a yield of 90% when equimolar amounts of 2,2-dimethyl-1-hydroxy-butan-3-one and triphenylphosphine, in a ten-fold amount of carbon tetrachloride, were heated for 12 hours under reflux. The solvent was distilled off, the residue was taken up in ether and the solution was filtered and distilled.

(c)

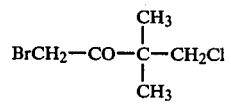

134.5 g (1 mol) of 1-chloro-2,2-dimethyl-butan-3-one were dissolved in 500 ml of ether. 51 ml (1 mol) of bromine were added dropwise at room temperature, with slight cooling, at a rate such that the bromine was steadily consumed. The solution was then stirred into 1,000 ml of ice-water and the organic phase was separated off, rinsed with 250 ml of water, dried over sodium sulphate and distilled. 169 g (80% of theory) of 1-bromo-4-chloro-3,3-dimethyl-butan-2-one of boiling point 95°–106° C./13 mm Hg were obtained.

(d)

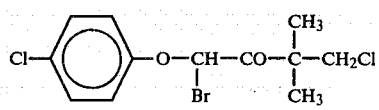

213 g (1 mol) of 1-bromo-4-chloro-3,3-dimethyl-butan-2-one were added dropwise to a boiling suspension of 128.5 g (1 mol) of 4-chlorophenol and 140 g (1 mol) of potassium carbonate in 1,000 ml of absolute acetone. The mixture was stirred for 15 hours under reflux and was then allowed to cool, and the inorganic residue was filtered off and rinsed with acetone. The filtrate was concentrated by distilling off the solvent in vacuo and the residue was taken up in 1,000 ml of methylene chloride, washed three times with 250 ml of water at a time, dried over sodium sulphate and distilled. 210 g (80.7% of theory) of 4-chloro-1-(4-chlorophenoxy)-3,3-dimethyl-butan-2-one of boiling point 125°–127° C./0.1 mm Hg were obtained.

210 g (0.81 mol) of 4-chloro-1-(4-chlorophenoxy)-3,3-dimethyl-butan-2-one were dissolved in 1,000 ml of carbon tetrachloride. 41 ml (0.81 mol) of bromine were added dropwise at room temperature at a rate such that the bromine was steadily consumed. The mixture was then stirred for 30 minutes at room temperature. After distilling off the solvent in vacuo, 268.3 g (98% of theory) of crude 1-bromo-4-chloro-1-(4-chlorophenoxy)-3,3-dimethyl-butan-2-one were obtained and were directly reacted further.

(e)

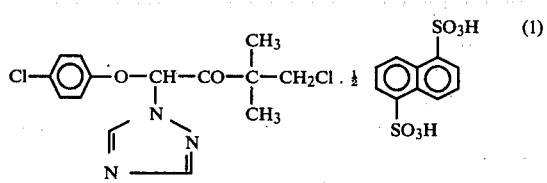

Process variant (a)

268.3 g (0.79 mol) of crude 1-bromo-4-chloro-1-(4-chlorophenoxy)-3,3-dimethyl-butan-2-one were dissolved in 2 l of absolute acetonitrile. 190 g (2.7 mol) of 1,2,4-triazole were added thereto and the mixture was heated for 20 hours under reflux. It was then concentrated by distilling off the solvent in vacuo and the residue was taken up in 1,000 ml of methylene chloride. The mixture was washed three times with 250 ml of water at a time, dried over sodium sulphate and again concentrated in vacuo. The oil which remained was dissolved in 1,000 ml of acetone and a solution of 140 g (0.48 mol) of naphthalenedisulphonic acid in 500 ml of acetone was added. After 30 minutes, the resulting precipitate was filtered off. 285 g (76.6% of theory) of 4-chloro-1-(4-chlorophenoxy)-3,3-dimethyl-1-(1,2,4-triazol-1-yl)-butan-2-one naphthalene-1,5-disulphonate of melting point 245° C. (with decomposition) were obtained.

EXAMPLE 2

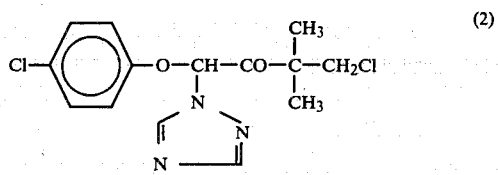

285 g (0.6 mol) of 4-chloro-1-(4-chlorophenoxy)-3,3-dimethyl-1-(1,2,4-triazol-1-yl)-butan-2-one naphthalene-1,5-disulphonate, obtained according to Example 1, were neutralized with aqueous sodium hydroxide solution. 221.7 g (67.5% of theory, relative to the 1-bromo-4-chloro-1-(4-chlorophenoxy)-3,3-dimethyl-butan-2-one employed) of 4-chloro-1-(4-chlorophenoxy)-3,3-dimethyl-1-(1,2,4-triazol-1-yl)-butan-2-one were obtained as a colorless oil having a refractive index $n_D^{20}$ of 1.546.

EXAMPLE 3

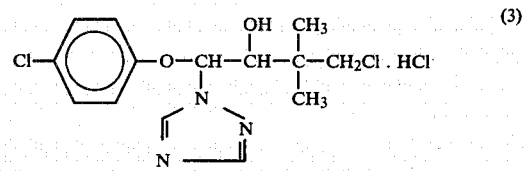

Process variant (b)

96.5 g (0.294 mol) of 4-chloro-1-(4-chlorophenoxy)-3,3-dimethyl-1-(1,2,4-triazol-1-yl)-butan-2-one [see Example 2] were dissolved in 300 ml of methanol. 12 g (0.3 mol) of sodiumm borohydride were introduced incrementally at 5° to 10° C.

The mixture was stirred for 15 hours at room temperature, 30 ml of concentrated hydrochloric acid were added and stirring was continued for 15 hours at room temperature. The reaction mixture was then stirred into 500 ml of saturated sodium bicarbonate solution and was extracted three times with 150 ml of methylene chloride each time, and the combined organic phases were washed twice with 100 ml of water each time, dried over sodium sulphate and concentrated in a waterpump vacuum by distilling off the solvent. The residue was dissolved in acetone, 100 ml of a solution of hydrogen chloride in ether were added and the mixture was concentrated in a waterpump vacuum. The residue was taken up in 100 ml of ethyl acetate and was allowed to crystallize out at 0° C. 41.4 g (38% of theory) of 4-chloro-1-(4-chlorophenoxy)-3,3-dimethyl-1-(1,2,4-triazol-1-yl)-butan-2-ol hydrochloride (erythro form and threo form) of melting point 157° C. were obtained.

EXAMPLE 4

(a)

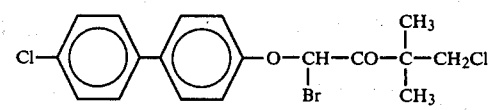

42.7 g (0.2 mol) of 1-bromo-4-chloro-3,3-dimethyl-butan-2-one were added dropwise to a boiling suspension of 41 g (0.2 mol) of 4-(4-chlorophenyl)-phenol and 28 g (0.2 mol) of potassium carbonate in 300 ml of absolute acetone. The mixture was stirred for 15 hours under reflux and was then allowed to cool and the inorganic residue was filtered off and rinsed with acetone. The filtrate was concentrated by distilling off the solvent in vacuo. The residue crystallized after the addition of 50 ml of diisopropyl ether. 37.5 g (55% of theory) of 4-chloro-1-[4-(4-chlorophenyl)-phenoxy]-3,3-dimethyl-butan-2-one of melting point 67°–68° C. were obtained.

33.7 g (0.1 mol) of 4-chloro-1-[4-(4-chlorophenyl)-phenoxy]-3,3-dimethyl-butan-2-one were dissolved in 250 ml of carbon tetrachloride. 5.1 ml (0.1 mol) of bromine were added dropwise at room temperature at a rate such that the bromine was steadily consumed. The mixture was then stirred for 30 minutes at room temperature. After distilling off the solvent in vacuo, crude 1-bromo-4-chloro-1-[4-(4-chlorophenyl)-phenoxy]3,3-dimethyl-butan-2-one was obtained in quantitative yield and was directly reacted further.

EXAMPLE 4

(b)

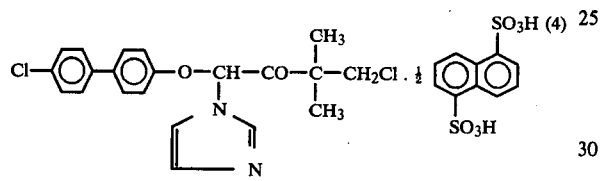

Process variant (a)

20.8 g (0.05 mol) of crude 1-bromo-4-chloro-1-[4-(4-chlorophenyl)-phenoxy]-3,3-dimethyl-butan-2-one were dissolved in 120 ml of absolute acetonitrile. 12 g (0.175 mol) of imidazole were added and the mixture was heated for 40 hours under reflux. It was then concentrated by distilling off the solvent in vacuo and the residue was taken up in 300 ml of methylene chloride. The solution was washed three times with 100 ml of water at a time and was dried over sodium sulphate and again concentrated in vacuo. The residue was taken up in 100 ml of acetone and a solution of 9 g (0.038 mol) of 1,5-naphthalenedisulphonic acid in 50 ml of acetone was added. After 2 hours, the precipitate formed was filtered off and dried. 19.6 g (72% of theory) of 4-chloro-1-[4-(4-chlorophenyl)-phenoxy]-3,3-dimethyl-1(imidazol-1-yl)-butan-2-one naphthalene-1,5-disulphonate of melting point 246° C. were obtained.

EXAMPLE 5

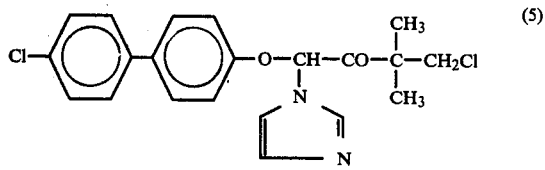

The 4-chloro-1-[4-(4-chlorophenyl)-phenoxy]-3,3-dimethyl-1-(imidazol-1-yl)-butan-2-one naphthalene-1,5-disulphonate obtained according to Example 4 was neutralized with sodium bicarbonate solution. 4-Chloro-1-[4-(4-chlorophenyl)-phenoxy]-3,3-dimethyl-1-(imidazol-1yl)-butan-2-one of melting point 97°–99° C. was obtained quantitatively.

EXAMPLE 6

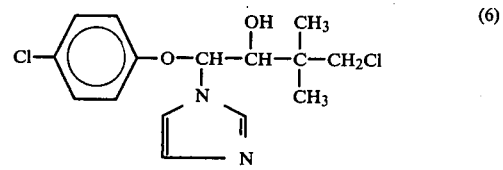

Process variant (b)

18.8 g (0.04 mol) of 4-chloro-1-(4-chlorophenoxy)-3,3-dimethyl-1-(imidazol-1-yl)-butan-2-one naphthalene-1,5-disulphonate [=Compound 15; prepared in accordance with Example 1, in 81% yield] were suspended in 100 ml of methylene chloride and 100 ml of sodium bicarbonate solution were added. The organic phase was separated off, dried over sodium sulphate and concentrated by distilling off the solvent in vacuo. The base thus obtained was taken up in 100 ml of isopropanol and 2 g (0.05 mol) of sodium borohydride were introduced incrementally at 5° to 10° C. The mixture was stirred for 15 hours at room temperature and the isopropanol was then distilled off. The residue was taken up in 100 ml of methylene chloride and, after adding 100 ml of water, was stirred for a further 15 hours at room temperature. The organic phase was then separated off, washed twice with 50 ml of water at a time, dried over sodium sulphate and concentrated. The oil which remained was boiled up in 100 ml of petroleum ether, which caused it to crystallize. 9.8 g (75% of theory) of 4-chloro-1-(4-chlorophenoxy)-3,3-dimethyl-1-(imidazol-1-yl)-butan-2-ol were obtained as an isomer mixture (erythro form and threo form) of melting point 120°–125° C.

The following compounds of the general formula

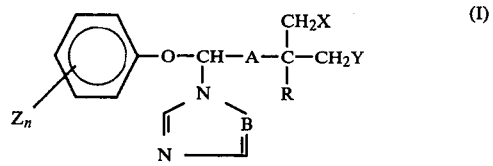

were obtained analogously to the foregoing examples:

TABLE 1

| Compound No. | $Z_n$ | A | X | Y | R | B | Melting point (°C.) |
|---|---|---|---|---|---|---|---|
| 7 | 4-⟨◯⟩-Cl | CO | H | Cl | CH₃ | N | 190 (decomposition) |

TABLE 1-continued

| Compound No. | $Z_n$ | A | X | Y | R | B | Melting point (°C.) |
|---|---|---|---|---|---|---|---|
| | | | | | | (x½ naphthalene-1,2-disulfonic acid) | |
| 8 | 4-⌬ (phenyl) | CO | H | Cl | CH₃ | N | 88–105 |
| 9 | 2,4-Cl₂ | CO | H | Cl | CH₃ | N | 63–64 |
| 10 | 4-NO₂ | CO | H | Cl | CH₃ | N | 105 |
| 11 | — | CO | H | Cl | CH₃ | N | 188–191 |
| | | | | | | (x½ naphthalene-1,2-disulfonic acid) | |
| 12 | — | CH(OH) | H | Cl | CH₃ | N | 94–99 |
| 13 | 4-Cl | CO | H | Br | CH₃ | N | 127–131 (x HCl) |
| 14 | 4-Cl | CH(OH) | H | Br | CH₃ | N | 120–122 |
| 15 | 4-Cl | CO | H | Cl | CH₃ | CH | 266–267 |
| | | | | | | (x½ naphthalene-1,5-disulfonic acid) | |
| 16 | 4-⌬ (phenyl) | CO | H | Cl | CH₃ | CH | 203–205 |
| | | | | | | (x½ naphthalene-1,5-disulfonic acid) | |
| 17 | 4-NO₂ | CO | H | Cl | CH₃ | CH | 273 |
| | | | | | | (x 1⅓ naphthalene-1,5-disulfonic acid) | |
| 18 | 2,4-Cl₂ | CO | H | Cl | CH₃ | CH | 244 |
| | | | | | | (½ naphthalene-1,5-disulfonic acid) | |
| 19 | 4-Cl | CO | H | Br | CH₃ | CH | 238–240 |
| | | | | | | (x½ naphthalene-1,5-disulfonic acid) | |
| 20 | 4-Cl | CO | Cl | Cl | CH₃ | CH | 245 |
| | | | | | | (x½ naphthalene-1,5-disulfonic acid) | |
| 21 | 4-Cl | CH(OH) | Cl | Cl | CH₃ | CH | 113–119 |
| 22 | 4-Cl | CO | Cl | Cl | CH₃ | N | 123–130 (x HCl) |
| 23 | 4-Cl | CH(OH) | H | Br | CH₃ | CH | 138–140 (geometric isomeric form) |
| 24 | 4-Cl | CO | H | Br | CH₃ | N | 223–25* |
| | | | | | | (x½ naphthalene-1,5-disulfonic acid) | |
| 25 | 4-⌬ (phenyl) | CO | H | Br | CH₃ | N | 105–08 |
| 26 | 4-⌬ (phenyl) | CO | H | Cl | CH₃ | N | 98–104 |
| 27 | 4-Cl,2-CH₃ | CO | H | Cl | CH₃ | N | 70 |
| 28 | 2,4-Cl₂ | CO | H | Cl | CH₃ | N | 124–31 (x HCl) |
| 29 | 2-Cl | CO | H | Br | CH₃ | N | 199–201 |

TABLE 1-continued

| Compound No. | $Z_n$ | A | X | Y | R | B | Melting point (°C.) |
|---|---|---|---|---|---|---|---|
| 30 | 2-Cl | CO | H | Cl | CH₃ | N | 210 ($x\frac{1}{2}$ naphthalene-1,5-disulfonic acid) |
| 31 | 4-Cl,2-CH₃ | CH(OH) | H | Cl | CH₃ | N | 104–10 ($x\frac{1}{2}$ naphthalene-1,5-disulfonic acid) |
| 32 | 2,4-Cl₂ | CH(OH) | H | Cl | CH₃ | N | 96–102 |
| 33 | 2-Cl | CH(OH) | H | Br | CH₃ | N | 132–40 (A-Form)* |
| 34 | 4-C₆H₅ | CH(OH) | H | Cl | CH₃ | N | 115–20 (A-Form) |
| 35 | 4-C₆H₅ | CH(OH) | H | Br | CH₃ | N | 147–50 |
| 36 | 2-Cl | CH(OH) | H | Cl | CH₃ | N | 132 (A-Form) |
| 37 | 4-Cl,2-CH₃ | CO | H | Cl | CH₃ | CH | 91 |
| 38 | 2,4-Cl₂ | CO | H | Cl | CH₃ | CH | 165–68 (x HCl) |
| 39 | 2-Cl | CO | H | Br | CH₃ | CH | 192–96 * |
| 40 | 2-Cl | CO | H | Cl | CH₃ | CH | 197 ($x\frac{1}{2}$ naphthalene-1,5-disulfonic acid) |
| 41 | 2-Cl | CH(OH) | H | Br | CH₃ | CH | 119–24 (A-Form)* ($x\frac{1}{2}$ naphthalene-1,5-disulfonic acid) |
| 42 | 4-Cl,2-CH₃ | CH(OH) | H | Cl | CH₃ | CH | 116–29 |
| 43 | 2,4-Cl₂ | CH(OH) | H | Cl | CH₃ | CH | 92–95 (A-Form) |
| 44 | 2-Cl | CH(OH) | H | Cl | CH₃ | CH | 97 (A-Form) |

\* = one of two possible geometric isomers

EXAMPLE 7

Precursors for use in step (d) of Example 1 can be prepared by the following alternatives for steps (b) and (c)

(a)

$$BrCH_2-CO-\underset{\underset{CH_3}{|}}{\overset{\overset{CH_3}{|}}{C}}-CH_2Br$$

34.8 g (0.3 mol) of 2,2-dimethyl-1-hydroxy-butan-3-one and, at 0° to 5° C., 40 ml (0.5 mol) of pyridine were added dropwise to 47.6 g (0.25 mol) of p-toluenesulphochloride in 100 ml of chloroform. The mixture was stirred for 15 hours at room temperature and was then poured onto 200 g of ice and 70 ml of concentrated hydrochloric acid. The organic phase was separated off, washed three times with 100 ml of water each time, dried over sodium sulphate and concentrated by distilling off the solvent in a waterpump vacuum. 200 ml of petroleum ether was added to the residue, whereupon 48 g (71% of theory) of 2,2-dimethyl-3-ketobutoxy-p-toluenesulphonic acid ester of melting point 49°–52° C. precipitated.

27 g (0.1 mol) of this p-toluenesulphonic acid ester were dissolved in 100 ml of methyl ethyl ketone and heated with 52 g (0.6 mol) of lithium bromide for 48 hours under reflux. The mixture was filtered, the solvent was distilled off under normal pressure, the residue was dissolved in methylene chloride and the solution was washed four times with 100 ml of water each time. The organic phase was dried over sodium sulphate and concentrated in a waterpump vacuum. 15 g (84% of theory) of 1-bromo-2,2-dimethyl-butan-3-one were obtained and this was reacted, analogously to 1-chloro-2,2-dimethyl-butan-3-one (see Example 1c), with bromine to give 1,4-dibromo-3,3-dimethyl-butan-2-one.

(b)

$$BrCH_2-CO-\underset{\underset{CH_3}{|}}{\overset{\overset{CH_2Cl}{|}}{C}}-CH_2Cl$$

Analogously to Example 1(a), 2,2-bis-hydroxymethylbutan-3-one was first prepared by formylation of methyl ethyl ketone; thereafter, the reaction of the 2,2-bis-hydroxymethyl-butan-3-one with two equivalents of N,N-diethyl-1,2,2-trichlorovinylamine to give 2,2-bis-chloromethyl-butan-3-one was carried out.

Finally, the 2,2-bis-chloromethyl-butan-3-one was then reacted with bromine to give 1-bromo-3,3-bis-chloromethylbutan-2-one.

The biological activity of the novel compounds can be seen in the following examples wherein the known comparison compounds have the following structures:

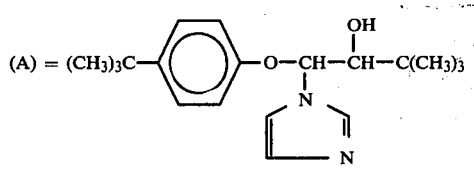
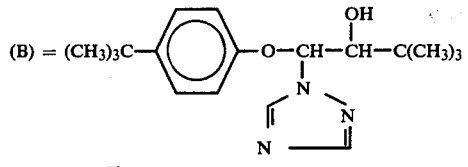
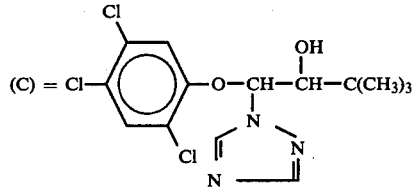
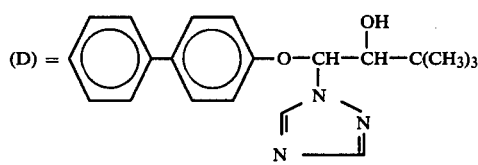
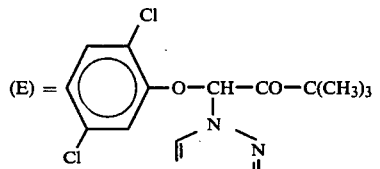
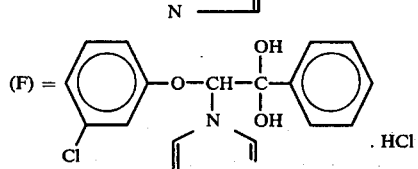
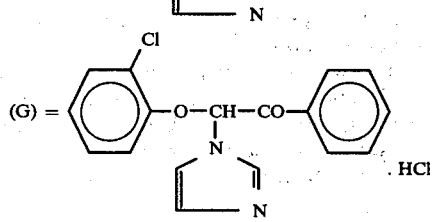
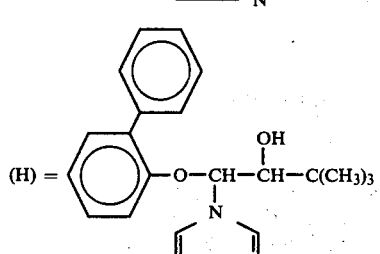
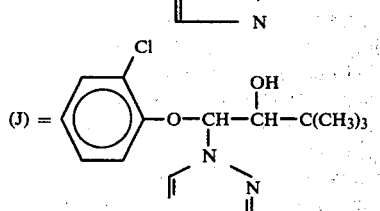

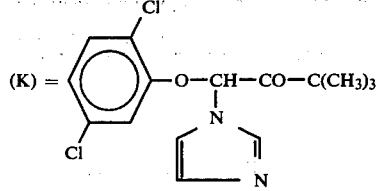
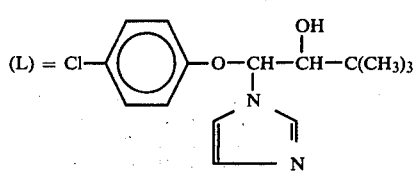
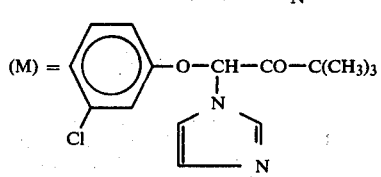
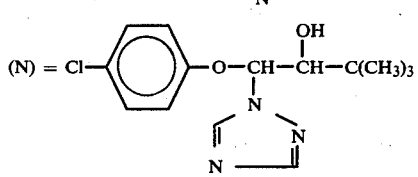
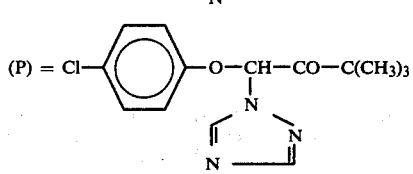
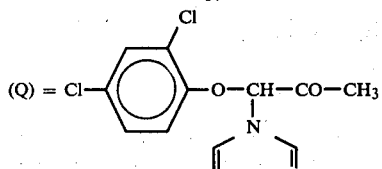

EXAMPLE 8

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were sprayed with the spray liquid until dripping wet. The plants remained in a greenhouse for 24 hours at 20° C. and at a relative atmospheric humidity of 70%. They were then inoculated by dusting the conidia of the apple powdery mildew causative organism (*Podosphaera leucotricha*) and placed in a greenhouse at a temperature of 21°-23° C. and at a relative atmospheric humidity of about 70%.

10 days after the inoculation, the infection of the seedlings was determined. The assessment data were converted to % infection. 0% meant no infection; 100% meant that the plants were completely infected.

The active compounds, the concentrations of the active compounds and the results can be seen from the following table:

TABLE 2

Podosphaera test (apple)/protective

| Active compound | Infection in % at an active compound concentration of | |
|---|---|---|
| | 0.01% | 0.0025% |
| (A) | 100 | — |
| (4) | — | 79 |
| (16) | — | 55 |
| (6) | — | 75 |
| (18) | — | 2 |

EXAMPLE 9

Erysiphe test (cucumbers)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoriacearusm*. The plants were subsequently placed in a greenhouse at 23°–24° C. and at a relative atmospheric humidity of about 75%.

After 12 days, the infection of the cucumber plants was determined. The assessment data were converted to percent infection. 0% meant no infection; 100% meant that the plants were completely infected.

The active compounds, the concentrations of the active compounds and the results can be seen from the following table:

TABLE 3

Erysiphe test (cucumbers)/protective

| Active compound | Infection in % at an active compound concentration of | |
|---|---|---|
| | 0.00062% | 0.0005% |
| (A) | 100 | — |
| (4) | —62 | — |
| (15) | — | 46 |
| (16) | — | 62 |
| (17) | — | 66 |
| (6) | — | 22 |
| (18) | — | 0 |

EXAMPLE 9

Erysiphe test (cucumbers)/systemic

Solvent: 4.7 parts by weight of acetone
Emulsifier: 0.3 part by weight of alkylaryl polyglycol ether
Water: 95 parts by weight The amount of active compound required to give the desired concentration of active compound in the watering liquid was mixed with the stated amount of solvent and the concentrate was diluted with the stated amount of water which contained the stated additives.

Cucumber plants grown in standard soil, in the 1–2 leaf stage, were watered three times within one week with 10 ml of the watering liquid, of the stated concentration of active compound, per 100 ml of soil.

The plants treated in this way were inoculated, after treatment, with conidia of the fungus *Erysiphe cichoracearum*. The plants were then set up in a greenhouse at 23°–24° C. and 70% relative atmospheric humidity. After 12 days, the infection of the cucumber plants was determined. The assessment data were converted to percent infection. 0% denoted no infection and 100% denoted that the plants were completely infected.

The active compounds, active compound concentrations and results can be seen from the table which follows:

TABLE 4

| Active compound | Erysiphe test/systemic (cucumbers) |
|---|---|
| | infection in % of the infection of the untreated control at an active compound concentration of 1 ppm |
| (D) | 100 |
| (C) | 100 |
| (1) | 27 |
| (10) | 75 |
| (11) | 6 |

EXAMPLE 11

Fusicladium test (apple)/(protective)

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

TABLE 5

Fusicladium test (apple)/protective

| Active compound | Infection in % at an active compound concentration of | |
|---|---|---|
| | 0.025% | 0.01% |
| (E) | 43 | — |
| (C) | — | 62 |

TABLE 5-continued

Fusicladium test (apple)/protective

| Active compound | Infection in % at an active compound concentration of | |
|---|---|---|
| | 0.025% | 0.01% |
| (1) | — | 11 |
| (7) | — | 16 |
| (8) | — | 0 |

EXAMPLE 12

Uromyces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated additives.

The young bean plants, which were in the 2-leaf stage, were sprayed with the spary liquor until dripping wet. The plants remained in a greenhouse for 24 hours at 20°-22° C. and a relative atmospheric humidity of 70% in order to dry. They were then inoculated with an aqueous uredospore suspension of the causative organism of bean rust (*Uromyces phaseoli*) and incubated for 24 hours in a dark humidity chamber at 20°-22° C. and 100% relative atmospheric humidity.

The plants were then set up in a greenhouse under intensive illumination for 9 days at 20°-22° C. and a relative atmospheric humidity of 70-80%.

10 days after the inoculation, the infection of the plants was determined. The assessment data were converted to % infection. 0% denoted no infection and 100% denoted that the plants were completely infected.

The active compounds, active compound concentrations and results can be seen from the following table:

TABLE 6

Uromyces test/protective

| Active compound | Infection in % of the infection of the untreated control at an active compound concentration (in %) of | |
|---|---|---|
| | 0.005 | 0.00025 |
| (A) | 71 | — |
| (6) | — | 84 |
| (16) | — | 10 |
| (4) | — | 29 |

EXAMPLE 12

Shoot treatment test/cereal mildew/protective/curative (leaf-destructive mycosis)

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

To test for curative activity the corresponding procedure was followed in converse sequence. The treatment of the single-leaved young barley plants with the preparation of active compound was carried out 47 hours after inoculation, when the infection, was already manifest.

After 6 days' dwell time of the plants at a temperature of 21°-22° C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows:

TABLE 7

Shoot treatment test/cereal mildew/protective/curative

| Active compound | Active compound concentration in the spray liquor in % by weight | Infection in % of the untreated control | |
|---|---|---|---|
| | | Protective | Curative |
| Untreated | — | 100.0 | 100.0 |
| (F) | 0.01 | 66.3 | — |
| (G) | 0.01 | — | 50.0 |
| (H) | 0.01 | — | 17.4 |
| (E) | 0.001 | 91.3 | — |
| (J) | 0.001 | 82.5 | — |
| (4) | 0.01 | 0.0 | 0.0 |
| (15) | 0.01 | 0.0 | 0.0 |
| (16) | 0.01 | 0.0 | 7.5 |
| (18) | 0.01 | 21.3 | — |
| (6) | 0.01 | 0.0 | 0.0 |
| (2) | 0.001 | 0.0 | — |
| (12) | 0.001 | 0.0 | — |
| (3) | 0.001 | 0.0 | — |
| (7) | 0.001 | 0.0 | — |
| (8) | 0.001 | 0.0 | — |
| (13) | 0.00025 | 21.3 | — |
| (14) | 0.00025 | 0.0 | — |

EXAMPLE 14

Powdery mildew of barley test (*Erysiphe graminis* var. *hordei*)/systemic (fungal disease of cereal shoots)

The active compounds were used as pulverulent seed treatment agents. They were prepared by extending the particular active compound with a mixture of equal parts by weight of talc and kieselguhr to give a finely pulverulent mixture of the desired concentration of active compound.

For the treatment of seed, barley seed was shaken with the mixture of active compound and extender in a closed glass bottle. The seed was sown at the rate 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had developed their first leaf, they were dusted with fresh spores of *Erysiphe graminis* var. *hordei* and grown further at 21°-22° C. and 80-90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

TABLE 8

Powdery mildew of barley test (*Erysiphe graminis* var. *hordei*)/systemic

| Active compounds | Active compound concentration in the dressing in % by weight | Amount of dressing used in g/kg of seed | Infection in % of the untreated control |
|---|---|---|---|
| Without dressing | — | — | 100.0 |
| (E) | 10 | 2 | 100.0 |
| (B) | 25 | 10 | 100.0 |
| (K) | 25 | 10 | 100.0 |
| (L) | 25 | 10 | 48.8 |
| (9) | 10 | 2 | 0.0 |
| (10 | 10 | 2 | 0.0 |
| (11) | 10 | 2 | 0.0 |
| (15) | 25 | 10 | 0.0 |
| (17) | 25 | 10 | 0.0 |
| (6) | 25 | 10 | 0.0 |

EXAMPLE 15

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

The active compounds, active compound concentrations in the spray liquor and degrees of infection can be seen from the table which follows:

TABLE 9

Shoot treatment test/cereal rust/protective

| Active compounds | Active compound concentration in the spray liquor in % by weight | Infection in % of the untreated control |
|---|---|---|
| Untreated | — | 100.0 |
| (B) | 0.025 | 75.0 |
| (M) | 0.025 | 90.0 |
| (1) | 0.025 | 8.8 |
| (7) | 0.025 | 0.0 |
| (9) | 0.025 | 33.8 |
| (10) | 0.025 | 41.3 |
| (11) | 0.025 | 50.0 |
| (2) | 0.025 | 0.0 |
| (12) | 0.025 | 0.0 |
| (3) | 0.025 | 0.0 |
| (13) | 0.025 | 8.8 |
| (14) | 0.025 | 0.0 |
| (4) | 0.025 | 0.0 |
| (15) | 0.025 | 40.0 |
| (18) | 0.025 | 0.0 |

EXAMPLE 16

Pyricularia and Pellicularia test

Solvent: 11.75 parts by weight of acetone
Dispersing agent: 6.75 parts by weight of alkylaryl polyglycol ether
Water: 987.50 parts by weight The amount of active compound required for the desired concentration of active compound in the spray liquid was mixed with the stated amount of the solvent and of the dispersing agent and the concentrate was diluted with the stated amount of water.

2×30 rice plants about 2–4 weeks old were sprayed with the spray liquid until dripping wet. The plants remained in a greenhouse at temperatures of 22° to 24° C. and a relative atmospheric humidity of about 70% until they were dry. Thereafter, some of the plants were inoculated with an aqueous suspension of 100,000 to 200,000 spores/ml of *Pyricularia oryzae* and placed in a chamber at 24° to 26° C. and 100% relative atmospheric humidity. The other plants were infected with a culture of *Pellicularia sasakii* grown on malt agar and were set up at 28° to 30° C. and 100% relative atmospheric humidity.

5 to 8 days after the inoculation, the infection of all the leaves present at the time of inoculation with *Pyricularia oryzae* was determined as a percentage of the untreated but also inoculated control plants. In the case of the plants infected with *Pellicularia sasakii*, the infection at the leaf sheaths after the same time was determined, again in relation to the untreated but infected control. The evaluation was made on a scale of from 1 to 9. 1 denoted 100% action, 3 denoted good action, 5 denoted moderate action and 9 denoted no action.

The active compounds, the concentrations of the active compounds and the results can be seen from the table which follows:

TABLE 10

Pyricularia (a) and Pellicularia (b) test

| Active compound | Infection in % of the infection of the untreated control at an active compound concentration of 0.025% | |
|---|---|---|
| | (a) | (b) |
| (N) | 9 | 9 |

TABLE 10-continued

Pyricularia (a) and Pellicularia (b) test

| Active compound | Infection in % of the infection of the untreated control at an active compound concentration of 0.025% | |
|---|---|---|
| | (a) | (b) |
| (1) | 3 | — |
| (8) | 3 | — |
| (2) | 5 | 1 | lium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

TABLE 11

Mycelium growth test

| Active compounds | Active compound concentration ppm | Fungi | | | | | | | | | | | | |
|---|---|---|---|---|---|---|---|---|---|---|---|---|---|---|
| | | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Pellicularia sasakii |
| | 10 | | | | | | | | | | | | | | |
| (P) | | 9 | 9 | — | — | 5 | 5 | 9 | 9 | 5 | — | 9 | 5 | 1 | 5 |
| (Q) | | 9 | 9 | 9 | 9 | 9 | 9 | 9 | 5 | 9 | 9 | 9 | 5 | 9 | 9 |
| (A) | | 9 | 9 | 9 | 9 | 9 | 9 | 9 | 9 | 9 | 9 | 5 | 9 | 9 | 9 |
| (1) | | — | 5 | — | — | 5 | 2 | — | 5 | 5 | — | 3 | 3 | 1 | — |
| (8) | | 5 | 5 | — | — | 5 | 5 | 5 | — | — | — | — | 3 | 1 | 5 |
| (9) | | — | 3 | — | — | 5 | 1 | — | 5 | — | — | 5 | 1 | 1 | — |
| (12) | | — | 5 | — | — | 3 | 2 | 5 | 5 | 3 | — | 1 | 5 | 1 | 5 |
| (3) | | 5 | 3 | — | — | 1 | 1 | 1 | 3 | 3 | — | 1 | 3 | 1 | 1 |
| (4) | | 3 | 3 | 3 | 5 | 1 | 3 | 2 | 3 | 5 | 3 | — | 5 | 1 | 3 |
| (15) | | 3 | 1 | 5 | 2 | 1 | 1 | 3 | 1 | 5 | 1 | 1 | 1 | 1 | 1 |
| (16) | | 1 | 1 | 1 | 1 | 1 | 1 | 1 | 1 | 5 | 1 | 1 | 1 | 1 | 1 |
| (17) | | — | 2 | — | — | 3 | 1 | — | 2 | 3 | — | 5 | 3 | 1 | 1 |
| (18) | | 3 | 1 | 5 | 1 | 1 | 1 | 1 | 1 | 1 | 1 | 2 | 1 | 1 | 1 |

EXAMPLE 18

Mycelium growth test

Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of DMF or acetone
  0.01 part by weight of emulsifier (alkylaryl polyglycol ether)
  1.80 parts by weight of water
Ratio of solvent mixture to nutrient medium;
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium which had been cooled to 42° C. and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the myce- It will be appreciated that the instant specification and examples are set forth by way of illustration and not limitation, and that various modifications and changes may be made without departing from the spirit and scope of the present invention.

What is claimed is:

1. 1-(azol-1-yl)-4-halo-1-phenoxy-butan-2-ones and -ols of the formula $$\text{Ph}(Z_n)-O-CH-A-\underset{R}{\overset{CH_2X}{\underset{|}{C}}}-CH_2Y$$
with N-B=N azole group in which
R represents alkyl with 1 to 4 carbon atoms;
X represents hydrogen, alkyl with 1 to 4 carbon atoms or halogen;
Y represents halogen;
Z represents halogen, straight-chain or branched alkyl with 1 to 4 carbon atoms, cycloalkyl with 5 to 7 carbon atoms, halogenoalkyl with 1 or 2 carbon atoms and 1 to 5 halogen atoms, alkoxy with one or 2 carbon atoms, alkylthio with 1 to 2 carbon atoms, alkoxycarbonyl with 1 to 5 carbon atoms in the alkoxy part, amino, cyano, nitro, phenyl or phenoxy substituted with at least one of halogen, amino, cyano, nitro and alkyl with 1 to 2 carbon atoms, phenylalkyl with 1 or 2 carbon atoms on the alkyl part optionally substituted in the alkyl part by alkylcarbonyl with a total of up to 3 carbon atoms and in the phenyl part by halogen, nitro or cyano;

n represents 0,1,2 or 3,

A is —CO— or CH(OH)—, and

B is —N= or —CH=, or an acid-addition salt thereof.

2. A compound according to claim 1, wherein such compound is 4-chloro-1-(4-chlorophenoxy)-3,3-dimethyl-1-(1,2,4-triazol-1-yl)-butan-2-one of the formula

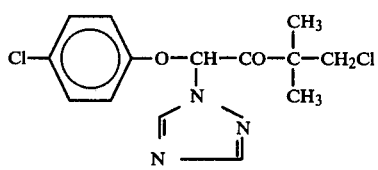

or an acid-addition salt thereof.

3. A compound according to claim 1, wherein such compound is 4-chloro-1-[4-(4-chlorophenyl)-phenoxy]-3,3-dimethyl-1-(1,2,4-triazol-1-yl)-butan-2-one of the formula

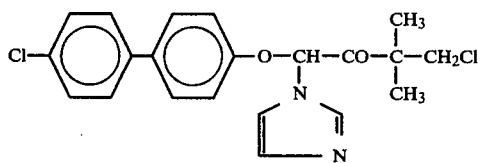

or an acid-addition salt thereof.

4. A compound according to claim 1, wherein such compound is 4-chloro-1-(4-chlorophenoxy)-3,3-dimethyl-1-(imidazol-1-yl)-butan-2-ol of the formula

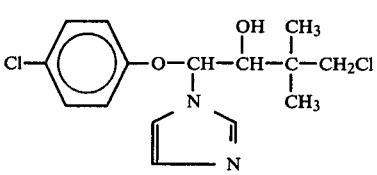

or an acid-addition salt thereof.

5. A compound according to claim 1, wherein such compound is 4-bromo-1-(4-chlorophenoxy)-3,3-dimethyl-1-(1,2,4-triazol-1-yl)-butan-2-one of the formula

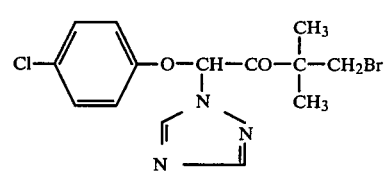

or an acid-addition salt thereof.

6. A fungicidal composition containing as active ingredient a fungicidally effective amount of a compound according to claim 1 in admixture with a diluent.

7. A method of combating fungi which comprises applying to the fungi, or to a habitat thereof, a fungicidally effective amount of a compound according to claim 1.

8. The method according to claim 1, wherein said compound is
4-chloro-1-(4-chlorophenoxy)-3,3-dimethyl-1-(1,2,4-triazol-1-yl)-butan-2-one,
4-chloro-1-[4-(4-chlorophenyl)-phenoxy]-3,3-dimethyl-1-(1,2,4-triazol-1-yl)-butan-2-one,
4-chloro-1-(4-chlorophenoxy)-3,3-dimethyl-1-imidazol-1-yl)-butan-2-ol or
4-bromo-1-(4-chlorophenoxy)-3,3-dimethyl-1-(1,2,4-triazol-1-yl)-butan-2-one,
or an acid-addition salt thereof.

9. The method according to claim 7, wherein the compound is applied to plants, seed or soil.

10. A compound according to claim 1, in which B is —N=.

* * * * *